United States Patent [19]

Sandler

[11] Patent Number: 5,025,104
[45] Date of Patent: Jun. 18, 1991

[54] 2,4-PENTANEDIONE-1-SULFONIC ACID AND METHOD FOR PREPARING THE SAME

[75] Inventor: Stanley R. Sandler, Springfield, Pa.

[73] Assignee: Atochem North America, Inc., Philadelphia, Pa.

[21] Appl. No.: 413,575

[22] Filed: Sep. 28, 1989

[51] Int. Cl.$^5$ .................. C07C 303/00; B01J 31/00
[52] U.S. Cl. .................................... 562/109; 502/168
[58] Field of Search ........................... 562/109, 102

[56] References Cited

U.S. PATENT DOCUMENTS 2,195,088  3/1940  Keppler .............................. 562/109
2,308,841  1/1943  Werntz ............................... 562/109

FOREIGN PATENT DOCUMENTS 0289952  11/1988  European Pat. Off. ............ 562/102

*Primary Examiner*—D. Alan Siegel
*Attorney, Agent, or Firm*—Panitch, Schwarze, Jacobs & Nadel

[57] ABSTRACT

2,4-pentanedionemonosulfonic acid is prepared by reacting chlorosulfonic acid with 2,4-pentanedione, preferably in the presence of an anhydrous solvent. The method of this invention generally yields 2,4-pentanedionemonosulfonic acid in excess of about 75 percent. The noval pentanedionesulfonic acid 2,4-pentanedionemonosulfonic acid(acetylacetone sulfonic acid) is disclosed.

2 Claims, No Drawings

2,4-PENTANEDIONE-1-SULFONIC ACID AND METHOD FOR PREPARING THE SAME

CROSS-REFERENCE TO RELATED APPLICATION

The present application is related to my copending U.S. patent application for "2,4-Pentanedione-1,5-Disulfonic Acid and Method for Preparing the Same," Ser. No. 413,793, filed concurrently herewith.

FIELD OF THE INVENTION

The present invention is directed to 2,4-pentanedionemonosulfonic acid (acetylacetone monosulfonic acid or 2,4-pentanedione-1-sulfonic acid) and methods for preparing the same.

BACKGROUND OF THE INVENTION

To the best of the inventor's belief, the literature is devoid of any information regarding 2,4-pentanedionemonosulfonic acid (2,4-pentanedionesulfonic acid).

Copending patent application Ser. No. 044,933, filed May 1, 1987, discloses the preparation of propanone-1,3-disulfonic acid (acetone disulfonic acid) by reacting chlorosulfonic acid with acetone (2-propanone). The disclosure of U.S. patent application Ser. No. 044,933 is incorporated herein by reference. As disclosed therein, the reaction of acetone with chlorosulfonic acid results in a diacid substitution at the first and third carbons.

Keto-substituted alkane sulfonic acids are useful as: 1) a esterification catalyst; 2) an alkylation catalyst; 3) a chelating agent; and 4) a starting material to give polymeric ion-exchange resins, among others. Such sulfonic acids are also useful in undergoing condensation reactions with other aldehydes and ketones because of their activated methylene groups. These reactions may lead to monomeric or polymeric compositions also having the uses described above. The very reactive methylene groups also allow these compounds to enolyze, thereby making them very useful in various substitution reactions involving electrophilic reagents.

SUMMARY OF THE INVENTION

The present invention is directed to the novel pentanedionesulfonic acid, 2,4-pentanedionemonosulfonic acid (acetylacetone sulfonic acid). In addition, the present invention is directed to a method of preparing 2,4-pentanedionemonosulfonic acid comprising reacting chlorosulfonic acid with 2,4-pentanedione. The reaction is preferably carried out in the presence of an anhydrous solvent, such as methylene chloride, and the viscous product may be separated from the solvent layer or it may be dissolved in water and then separated. 2,4-pentanedione-1,5-disulfonic acid is produced as a by-product of the method disclosed herein.

DETAILED DESCRIPTION OF THE PREFERRED EMBODIMENTS

According to the present invention, 2,4-pentanedionemonosulfonic acid (acetylacetone sulfonic acid) is prepared by reacting chlorosulfonic acid with 2,4-pentanedione (acetylacetone) in the presence or absence of solvents. Copending patent application Ser. No. 044,933 disloses, as stated above, the preparation of propanone-1,3-disulfonic acid by reacting chlorosulfonic acid with acetone. Substituting 2,4-pentanedione (acetylacetone) for acetone (2-propanone) in that reaction, one skilled in the art would expect a similar diacid substitution, especially where there is a stoichiometric excess of chlorosulfonic acid. Where 3.0 or more moles of chlorosulfonic acid are reacted per mole of 2,4-pentanedione, tri- or polysulfonic acids would be expected. Surprisingly, however, the monosulfonic acid results when using 2,4-pentanedione, even if two moles of chlorosulfonic acid are used per mole of 2,4-pentanedione.

In addition, because the third carbon of pentanedionesulfonic acid is the most reactive (enolyzable), one skilled in the art would expect that a monosulfonic acid resulting from the reaction between 2,4-pentanedione and chlorosulfonic acid would be the 2,4-pentanedione-3-sulfonic acid. However, surprisingly, the monosulfonic acid resulting from this reaction is 2,4-pentanedionesulfonic acid where the sulfonic acid group is at the 1 position. Further, any disulfonic acid formed in the reaction between 2,4-pentanedione and chlorosulfonic acid would be expected to be the 2,4-pentanedione-1,3-disulfonic acid. Instead, however, the 1,5-disulfonic acid results.

The reaction of the method according to the present invention may be represented by the following equation:

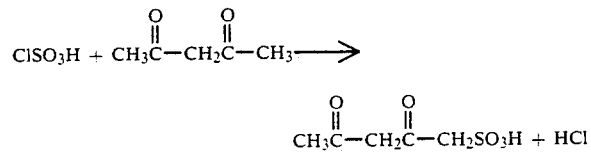

The reaction is exothermic and proceeds rapidly with only slight to moderate warming of the reaction mixture. Hydrogen chloride is formed as a by-product and is liberated during the reaction. When HCl liberation ceases, the reaction is complete.

Because chlorosulfonic acid reacts vigorously with water, it is preferred that the reactants and the reaction conditions be substantially anhydrous. For example, the primary impurities in chlorosulfonic acid are hydrochloric and sulfuric acids, which form from contamination with water. The chlorosulfonic acid is preferably about 99–100% grade, which is readily available commercially from several sources. 2,4-pentanedione is also available commercially and the 100%, anhydrous grade is preferred.

The reaction of the present invention may be carried out neat or in the presence of a solvent for the reactants. The use of a solvent is preferred, although not necessary, because the neat reaction becomes quite viscous and difficult to stir. In addition, the use of a solvent facilitates separation of unreacted reactants. For example, the product phase separates readily when methylene chloride is used as the solvent. The unreacted starting materials remain dissolved in the methylene chloride which can be separated from the product.

The solvent may be virtually any inert solvent which readily dissolves the reactants. Examples of suitable solvents include methylene chloride, carbon tetrachloride, 1,1,1-trichloroethane (methyl chloroform), chloroform, dioxane, acetonitrile, tetrahydrofuran and ethyl ether. The presently preferred solvent is methylene chloride. Other suitable solvents for use in the method according to the present invention will be evident to those skilled in the art in view of this disclosure.

While the order of addition of the reactants is not particularly critical, it is presently preferred to dissolve 2,4-pentanedione in a solvent (where desired) and then add the resulting solution to chlorosulfonic acid in the reaction vessel.

The reaction proceeds readily at substantially atmospheric pressure, preferably under a dry air atmosphere, with simple agitation (e.g., stirring). Noticeable phase separation occurs throughout the reaction, and the evolved hydrogen chloride gas may be captured by conventional means.

The reaction temperature of the process is generally about 4° to about 50° C., and preferably about 4° to about 40° C., unless the reaction is carried out under pressure. The upper end of the temperature range is generally limited by the lowest boiling component of the reaction mixture. For example, where methylene chloride is used as a solvent, the reaction at atmospheric pressure would be carried out up to its boiling point of about 40° C. Similarly, where a carbon tetrachloride is used as a solvent (b.p. 76°), heating up to about 76° C. may be used. In any event, the temperature of the reaction should not exceed about 140.5° C. (b.p. of 2,4-pentanedione; chlorosulfonic acid b.p. about 158° C.) at 1 atmosphere where no solvent having a lower boiling point is used. However, above 50° C., the yield of the 2,4-pentanedionesulfonic acid decreases, while by-product formation of the 2,4-pentanedione-1,5-disulfonic acid increases.

Generally, to accelerate the reaction, the reactants can, in solution, be refluxed for three to four hours.

The reactants are generally present with a slight stoichiometric excess of chlorosulfonic acid. In particular, the molar ratio of chlorosulfonic acid to 2,4-pentanedione is preferably about 1.5:1 to about 2.5:1. A ratio of about 2:1 is presently preferred, although one skilled in the art will appreciate that higher and lower molar ratios may be used in accordance with the present invention.

Any unreacted chlorosulfonic acid may be recovered from the solvent, if and where desired. It is also preferred that the amount of solvent be kept to a minimum, consistent with optimum mixing, handling and reaction conditions.

The 2,4-pentanedionemonosulfonic acid resulting from the method of the present invention may be recovered by separation or by dissolving in water. It is preferred to separate the solvent first to remove unreacted starting materials and thus minimize the amount of hydrochloric acid and sulfuric acid by-products formed by the hydrolysis of unreacted chlorosulfonic acid present in the aqueous product.

The product (which is typically yielded in excess of 75% using the method of this invention) may be conveniently stored as an anhydrous liquid or as an aqueous solution.

The present invention will now be illustrated in further detail by reference to the following specific, non-limiting examples. In the examples, proton ($H^1$) and carbon ($C^{13}$) nuclear magnetic resonance (NMR) analyses were used to identify the product. The solvents for the NMR analyses were deuterated dimethyl sulfoxide ($D_6DMSO$) and deuterium oxide ($D_2O$) with trimethylsilane (TMS) as the internal standard.

EXAMPLE 1

70.0 g (0.60 mole) of chlorosulfonic acid (99%) and 200 ml methylene chloride were added to a 500 ml 3-necked round-bottom flask equipped with a dry-ice condenser, a thermocouple in glass tube, mechanical stirrer, gas outlet, and dropping funnel. 30.0 g (0.3 mole) 2,4-pentanedione (100% anhydrous) were added drop-wise at a rate so as to maintain the temperature of the reaction mixture below about 20° C. When addition was complete, the clear homogeneous solution was warmed to about 38°-40° C. (reflux at 40° C.). A vigorous evolution of hydrogen chloride began at about 35° C. with refluxing of the methylene chloride. After another 15-30 minutes, a lower layer of product (oil) began to appear and the reaction was allowed to continue for another 3-4 hours. The product was separated from the methylene chloride layer with $H_2O$ and, after drying, weighed 65.0 g. Titration of the methylene chloride layer indicated that about 0.15 mole of chlorosulfonic acid remained unreacted.

$H^1$ NMR and $C^{13}$ NMR analyses indicated the following which were consistent with the structure of 2,4-pentanedionemonosulfonic acid.

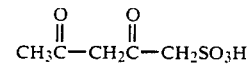

| $H^1$ NMR Proton Assignment | Chemical Shifts (ppm) $D_6DMSO$ Solvent | |
|---|---|---|
| C# | | |
| $CH_3—$ | 1.95 | Singlet |
| $C(=O)—\underline{CH_2}—C(=O)$ | 3.95 | Singlet |
| $C(=O)—\underline{CH_2}—SO_3H$ | 3.97 | Singlet |
| $—SO_3H$ | 12.95 | Singlet |
| $C^{13}$ NMR Carbon Assignment | Chemical Shifts (ppm) $D_6DMSO$ Solvent | |
| C# | | |
| $CH_3—\underline{C(=O)}$ | 194.6 | Singlet |
| $CH_2—\underline{(C=O)}—CH_2$ | 171.7 | Singlet |
| $C(=O)—\underline{CH_2}—C(=O)$ | 63.4 | Triplet |
| $C(=O)—\underline{CH_2}—SO_3H$ | 63.4 | Triplet |
| $CH_3—$ | 21.0 | Quartet |

The NMR spectra are consistent with the major product as being

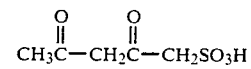

EXAMPLE 2

104.9 g (0.90 mole) chlorosulfonic acid (99%) and 200 ml methylene chloride were added to a 500 ml 3-necked round-bottom flask equipped as in Example 1. 30.0 g (0.30 mole) 2.4-pentaedione were then added drip-wise at a rate so as to maintain the temperature of the reaction mixture below about 20° C. When the addition was complete, the clear homogeneous solution was warmed to about 38°-40° C. (reflux at 40° C.). A vigorous evolution of hydrogen chloride began and the solution turned turbid during reflux. After another 15 to 30 minutes of the reaction, a lower viscous layer of product began to appear and the reaction was allowed to continue for about 3—4 hours. The methylene chloride was removed by decantation and 200 ml of fresh methylene chloride were added. 100 g water was then added drop-wise to form an aqueous solution of the product, which separated from the methylene chloride. The weight of the product layer was 190.0 g. The H¹ NMR and C¹³ NMR indicated essentially the same results as shown in Example 1 and was consistent with the composition as being mainly

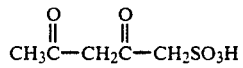

The results of Example 2 illustrate that chlorosulfonic acid in excess of that used in Example 1 is not necessary and that the major product is surprisingly only the monosulfonic acid.

EXAMPLE 3

The procedure of Example 1 was repeated, except that the 2,4-pentanedione was dissolved in an equal weight of methylene chloride before adding it to the chlorosulfonic acid. The reaction gave substantially the same results as found in Example 1 with 2,4-pentanedionesulfonic acid as the product.

The present invention may be embodied in other specific forms without departing from the spirit or essential attributes thereof and, accordingly, reference should be made to the appended claims, rather than the specification, as indicating the scope of the invention.

I claim:
1. 2,4-pentanedione-1-sulfonic acid.
2. 2,4-pentanedione-1-sulfonic acid prepared by reacting chlorosulfonic acid with 2,4-pentanedione.

* * * * *